US008282928B2

(12) United States Patent
Sunwoo et al.

(10) Patent No.: US 8,282,928 B2
(45) Date of Patent: Oct. 9, 2012

(54) ANTI-GLUTEN EGG YOLK ANTIBODIES FOR THE TREATMENT OF CELIAC DISEASE

(75) Inventors: Hoon Sunwoo, Edmonton (CA); Jeong Sim, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 309 days.

(21) Appl. No.: 12/779,622

(22) Filed: May 13, 2010

(65) Prior Publication Data

US 2011/0008362 A1 Jan. 13, 2011

Related U.S. Application Data

(63) Continuation-in-part of application No. 10/599,660, filed on May 30, 2007, now Pat. No. 7,854,942.

(51) Int. Cl.
*A61K 39/395* (2006.01)

(52) U.S. Cl. ..................................... 424/157.1

(58) Field of Classification Search .......................... None
See application file for complete search history.

(56) References Cited

U.S. PATENT DOCUMENTS

| | | | |
|---|---|---|---|
| 4,357,272 A | 11/1982 | Polson | |
| 4,550,019 A | 10/1985 | Polson | |
| 4,748,018 A | 5/1988 | Stolle et al. | |
| 5,080,895 A | 1/1992 | Tokoro | |
| 5,367,054 A | 11/1994 | Lee | |
| 5,849,349 A | 12/1998 | Stolle et al. | |
| 2008/0003263 A1 | 1/2008 | Sunwoo et al. | |

FOREIGN PATENT DOCUMENTS

| | | |
|---|---|---|
| CA | 2267421 | 10/1997 |
| CA | 2561800 | 10/2005 |
| EP | 0905518 | 9/1997 |
| WO | 0002582 | 1/2000 |
| WO | 03104273 | 6/2003 |
| WO | 2005099753 | 10/2005 |

OTHER PUBLICATIONS

Saalman, R. et al.; Antibody-Dependent Cell-Mediated Cytotoxicity to Gliadin=Coated Cells with Sera from Children with Coeliac Disease; Scandinavian Journal of Immunology; 1998; vol. 47; pp. 37-42; Blackwell Science Ltd.

Alaedini, A. et al.; Narrative Review: Celiac Disease: Understanding a Complex Autoimmune Disorder; Annals of Internal Medicine; 2005; vol. 142, No. 4; pp. 289-298; American College of Physicians.

Fasano, Allessio et al.; Current Approaches to Diagnosis and Treatment of Celiac Disease: An Evolving Spectrum; Article XP-002478096; Gastroenterology; 2001; pp. 636-651.

Ora Mune Magna; Immune Therapy Research Laboratory; 2008; Internet; www.oramune.com.

Ellis, H.J. et al.; Measurement of Gluten Using a Monoclonal Antibody to a Coeliac Toxic Peptide of A Gliadin; gut.bmj.com; 2008; vol. 43; pp. 190-195.

*Primary Examiner* — Sharon Wen
(74) *Attorney, Agent, or Firm* — Bennett Jones LLP

(57) ABSTRACT

The present invention relates to compositions for ameliorating the symptoms of celiac disease or gluten sensitive enteropathy comprising egg yolk antibodies against gluten, including gliadin, high molecular glutenin, low molecular glutenin and mixtures of the three peptides. The antibodies may be produced by immunizing laying hens with immunogenic preparations of gluten and harvesting the eggs and egg yolks.

12 Claims, 3 Drawing Sheets

ANTI-GLUTEN EGG YOLK ANTIBODIES FOR THE TREATMENT OF CELIAC DISEASE

CROSS REFERENCE TO RELATED APPLICATIONS

This application is a Continuation-In-Part application of co-pending U.S. patent application Ser. No. 10/599,660 filed on Apr. 18, 2005, which claimed priority from U.S. Provisional Patent Application 60/521,394 filed on Apr. 16, 2004.

FIELD OF THE INVENTION

The present invention generally relates to pharmaceutical or nutraceutical compositions comprising anti-gluten antibodies and methods for producing and using such antibodies. The compositions may comprise whole egg yolk, or processed egg yolk, or isolated or purified fractions of the egg yolk, and may be used in the active or prophylactic treatment of celiac disease.

BACKGROUND OF THE INVENTION

Celiac disease (also known as celiac sprue, non-tropical sprue or gluten-sensitive enteropathy) is a common autoimmune condition triggered by ingesting wheat proteins called gluten. In cereal grains and flour, such as wheat, rye or barley, gluten is a complex mixture of proteins including alcohol-soluble monomers called gliadins and alcohol-insoluble polymers called glutenins. Gliadins can be divided into alpha, gamma and omega types on the basis of their amino acid sequences and mobility on electrophoresis. The glutenin subunits can be divided into high molecular weight (HMG) and low molecular weight (LMG) groups.

The clinical spectrum of gluten sensitivity includes typical celiac disease associated with the classical features of fatigue, chronic diarrhoea, malabsorption of nutrients, weight loss, abdominal distension, anaemia, as well as a failure to thrive in young children.

The typical form of celiac disease has an incidence of approximately 1 in 2500 in people of European descent, and also occurs in North African and Asian populations in lower incidence. The atypical form is also found in those who have latent onset of the disease. In total, the incidence of typical and atypical forms is about 1 in 1500. Asymptomatic celiacs are discovered when relatives of celiacs are tested. Latent celiacs are defined as those who have one of the companion diseases such as other autoimmune disorders such as diabetes, arthritis, Sjogren's syndrome, thyroid disease, collagen vascular disease, and liver disease. When combined, these various presentations of celiac disease reach as high as 1 in 300.

In celiac patients, gluten triggers an auto-immune attack. The ingested gluten carries epitopes capable of activating T cells, so the process can be considered to be an autoimmune disease.

There are two major components leading to the disease: a genetic background and environmental factors that will trigger the disease to a full expression of typical or atypical symptoms.

The large majority of celiac patients express human leukocyte antigen HLA-DQ2 or DQ8 molecules, or both. Enterocytes, cells on the lining of the small intestine, have receptors which are 'programmed' by the Class II antigens to recognize gluten. The gluten binds to HLA receptors that are present on the enterocytes. When this binding occurs, there is a migration to the other side of the cells. This receptor-gluten complex can reach cells in the bloodstream. There are lymphocytes that are responsible for the production of toxic compounds that are ultimately responsible for tissue damage in the intestine. Among them, T helper I cells and cytokines apparently play a major role in a local inflammatory process and also stimulate B-cells differentiation in plasma cells producing antibodies.

Currently, the only acceptable treatment for celiac disease is strict adherence to a 100% gluten-free diet for life. An adherence to a gluten-free diet can prevent almost all complications caused by the disease. A gluten-free diet means avoiding all products that contain wheat, rye and barley, or any of their derivatives, for example in commercial soups, sauces, ice creams, hot dogs, and other foods.

However, this is a difficult task as there are many hidden sources of gluten found in the ingredients of many processed foods. Many commercial products, ready meals and convenience foods are made with wheat flour, gluten-containing wheat proteins or gluten-containing starches added as fillers, stabilizing agents or processing aids. These include sausages, fish fingers, cheese spreads, soups sauces, mixed seasonings, mincemeat for mince pies, and some medications and vitamin supplements. Another possible source of contamination of gluten-free products occurs when they are produced using the same production lines and equipment employed for making gluten-containing foods.

In view of the serious and widespread nature of celiac disease, natural methods of treating or ameliorating the effects of the disease are needed. The present invention is directed to addressing such a need.

SUMMARY OF THE INVENTION

The present invention is directed at pharmaceutical or nutraceutical compositions for treating celiac disease or preventing or ameliorating the symptoms of celiac disease, comprising naturally occurring egg yolk components. In one embodiment, the compositions of the present invention comprise at least one egg yolk antibody to gluten proteins and essential nutrients in egg yolk for treatment of patients with celiac disease.

The antibody used in the compositions may include polyclonal antibodies which have a masking activity against gluten proteins such as gliadin, high molecular glutenin, (HMG) and low molecular glutenin (LMG) found in wheat flour, and which act as a modulator of permeability in intestinal epithelium in those suffering from celiac disease.

The antibodies are produced by immunizing fowl with gluten proteins and harvesting their eggs. Gluten proteins for immunization are produced by isolating the gliadin, HMG and LMG from wheat flour. The gliadin fraction is isolated from wheat flour by defatting the flour, removing starch, and then extracting gliadin fraction with alcohol. The glutenin fractions are isolated from wheat flour by defatting flour, removing starch, and then extracting glutenin fractions with a reducing agent.

The antibody preparations may comprise polyclonal antibodies directed at one of the components of gluten, gliadin, HMG or LMG. Alternatively, the antibody composition may comprise a cocktail of polyclonal antibodies directed at combinations of gliadin, HMG or LMG.

In one embodiment, the polyclonal antibodies may comprise a chicken anti-gliadin polyclonal antibody, which is prepared by immunizing a chicken with gliadin fractions, followed by collecting eggs from the immunized chicken, and separating egg yolk from the egg white.

In another embodiment, the polyclonal antibodies may comprise chicken anti-gliadin, HMG and LMG polyclonal antibodies by immunizing a chicken with fractions of gliadin, HMG and LMG, followed by collecting eggs from the immunized chicken, and separating egg yolk from the egg white.

Therefore, in one aspect, the invention may comprise a therapeutic composition for treating celiac disease or gluten sensitive condition comprising anti-gluten egg yolk antibodies.

In another aspect, the invention may comprise the use of egg yolk comprising anti-gluten antibodies in the preparation of a medicament or food product for the treatment or prevention of celiac disease or gluten sensitive condition.

In yet another aspect, the invention may comprise the use of anti-gluten antibodies purified or partially purified from egg yolk in the preparation of a medicament or food product for the treatment or prevention of celiac disease or gluten sensitive condition.

In another aspect, the invention may comprise a method of treating, preventing, or ameliorating the symptoms of celiac disease or a gluten sensitive condition comprising the step of administering to a mammal in need thereof a pharmaceutical or nutraceutical composition or food product comprising egg yolk comprising anti-gluten antibodies.

In another aspect, the invention may comprise a method of preventing gluten uptake in the digestive system of a mammal comprising the steps of administering to the mammal a pharmaceutical or nutraceutical composition or a food product comprising avian anti-gluten antibodies.

BRIEF DESCRIPTION OF THE DRAWINGS

The invention will now be described by way of exemplary embodiments with reference to the accompanying drawings. In the drawings.

DETAILED DESCRIPTION OF THE INVENTION

The present invention provides for pharmaceutical or nutraceutical compositions for treating patients with celiac disease, or ameliorating their symptoms. When describing the present invention, all terms not defined herein have their common art-recognized meanings.

The term "antibody" includes polyclonal and monoclonal antibodies. Avian yolk antibodies have been reported to exhibit useful properties for both research and clinical applications as mammalian antibodies do (see, for example, U.S. Pat. Nos. 5,340,923; 5,585,098; 5,601,823; and 5,976,519). Egg yolks derived from a laying hen are inexpensive and more convenient and safer to handle as compared to the hyperimmunized mammalian sera. More importantly, yolk antibodies are able to stand up to the scrutiny under modern animal protection regulations (A. Polson et al., Immunol. Commun. 9:475 (1980); and B. Gottstein et al.). These facts suggest a potential use of egg yolk as a commercial source of antibodies. Immunoglobulin Y (IgY) is an avian immunoglobulin.

As used herein, the term "anti-gluten antibodies" refers to antibodies which specifically bind to at least one epitope in gluten, which may include gliadin, HMG or LMG. In one embodiment, anti-gluten antibodies comprises a cocktail of antibodies specific to different components of gluten.

The therapeutic effect of the present invention is mediated by blocking glutens contained in foodstuffs before they are transported across the epithelial layer in intestines. With typical celiac disease, intact gluten is permeated into mucosal membrane without digestion. By binding to gluten with anti-gluten antibodies, gluten is passed through the intestines, rather than being transported into the mucosal membrane, thereby preventing the disease-causing toxicity. The present invention may also be beneficial for gluten-sensitive people who are essentially asymptomatic or have no gastrointestinal symptomalogy.

Figure 1:
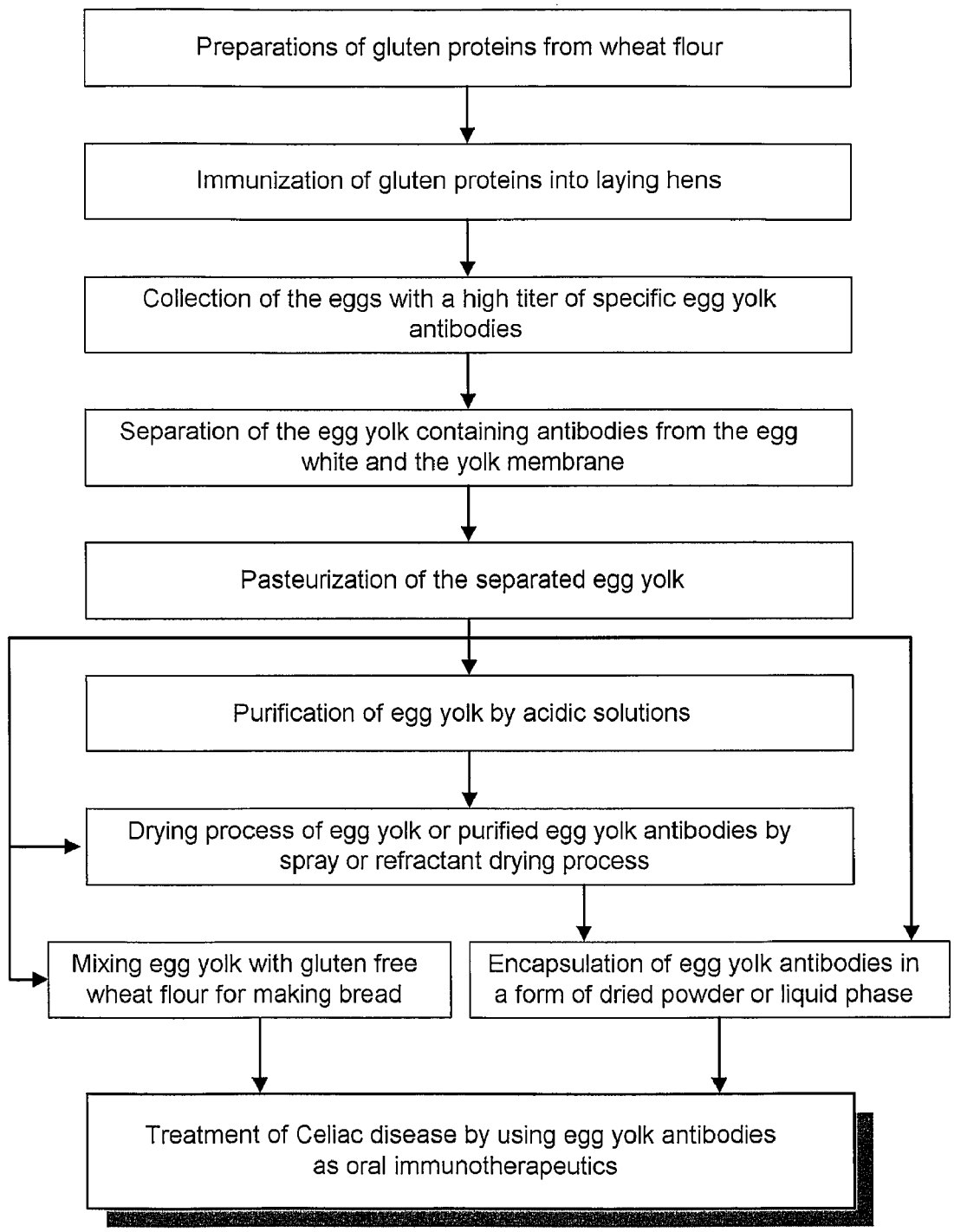
FIG. 1 is a block diagram showing a process of producing antibodies against gluten proteins and preparing antibodies for the treatment of celiac disease, according to the present invention.

A method of producing anti-gluten (gliadin, HMG and LMG) antibodies is shown schematically in FIG. 1. The process comprises the steps of preparing antigenic materials from wheat flour, injecting the antigenic materials into egg-laying fowl, which may include ducks or hens, and selecting the eggs containing a high titer of egg yolk antibodies. Preferably, the eggs are further processed by separating the egg yolks from egg white and purifying egg yolk antibodies. The egg yolk containing antibody may be used as a food ingredient in the same manner as conventional egg yolks. For example, the egg yolk (or whole eggs) may be mixed with gluten free flour or normal wheat flour for making bread or be mixed with foods such as ice cream, coffee cream, mayonnaise, margarine, and salad dressing which use egg yolk as an emulsifier. Furthermore, the egg yolk, or purified or partially purified fractions of the egg yolk, may be formed into pharmaceutical or nutraceutical formulations for treating patients with celiac disease.

Gluten proteins may be prepared from wheat flour as described by Verbruggen et al. (Journal of Cereal Science, 1998, 28:25-32). Gliadin, HMG or LMG may each be isolated from wheat flour to be used as an antigenic material. It is preferable to enhance the immunogenicity of the gluten proteins by employing well-known adjuvants such as Freund's incomplete adjuvant or a flax oil, or other oil/water emulsions. The specific formulation of the antigenic material is not an essential element of the present invention.

The antigenic preparations are injected into laying fowl, such as hens, preferably at various intervals, to induce an immune response. The hens may be injected intra-muscularly or subcutaneously. The specific mode of injection is not an essential element of the present invention. It is well known that the IgY antibodies produced by the hens in response to such an immunochallenge are transferred and concentrated in the egg yolk.

Once the eggs are harvested, the eggs may be further processed to isolate the egg yolk, which itself may be further processed. The liquid egg yolk may be encapsulated or otherwise used in oral dosage forms. The egg yolk may be dried by spray or refractant drying method, and the resulting dried powder may be encapsulated or otherwise used in oral dosage forms.

Alternatively, a procedure of partial purification or fractionation may be carried out to remove the majority of the non-aqueous bio-molecules and granules and preferably the majority of other proteins in the egg yolk. Any conventional method effective to achieve such a purpose is useful in the present invention, exemplary of which includes the use of PEG, dextran sulfate or a natural gum, such as sodium alginate, carrageenan and xanthan gum, to coprecipitate the undesired substances, and the use of an aqueous buffer or water to obtain an aqueous phase rich with antibodies.

In a preferred embodiment of the present invention, the yolk is firstly separated from the egg white, and then washed with distilled water to remove as much albumen as possible. The vitelline membrane encasing the yolk is punctured, and the separated yolk fraction is then diluted with an effective amount of an aqueous buffer or water to form a suspension of the egg yolk. Preferably, the collected egg yolk is diluted with an aqueous buffer solution or distilled water in a ratio of about 1:2 to about 1:40 v/v, and more preferably, in a ratio of about 1:5 to about 1:30 v/v. pH value is reported to be a critical factor during the stage of partial purification (E. M. Akita and S. Nakai, J. Food Sci. 57:629 (1993)). For efficient recovery of yolk antibodies, pH is preferably set within a range of about 5-7. Desirably, the temperature in this step is within a range of about 0° C. to about 60° C. The suspension of the egg yolk is gently agitated to form a homogenous mixture, and then allowed to stand for a period of time sufficient to form the aqueous and non-aqueous phases. The water insoluble materials, including non-aqueous bio-molecules such as lipoproteins, phospholipids, sterols and the like, are then removed from the aqueous yolk suspension by centrifugation. The resulting antibody-containing supernatant may then be separated from the viscous precipitant by decanting, suctioning, or other like methods known in the art.

Optionally, the yolk supernatant is further treated with a high concentration of a non-denaturing salt to induce precipitation of the antibodies. Examples of the salts useful for precipitation of the yolk antibodies include but are not limited to NaCl, $Na_2SO_4$, $(NH_4)_2SO_4$, KCl, $CaCl_2$, and $MgSO_4$. Preferred salts include $Na_2SO_4$ and $(NH_4)_2SO_4$. The salt concentration for precipitating antibodies is important and, depending on the type of the salt, is usually present in an amount of higher than 15% and lower than 35% by weight, preferably in a range between 20% and 30% by weight of the salt, on the basis of the final volume of the yolk supernatant.

Alternatively, the antibodies may be purified or isolated using any conventional technique such as by immunoaffinity purification.

In the present invention, the compositions for treating patients with celiac disease may include formulations of egg yolk containing specific antibodies for oral administration. In particular, in addition to pharmaceutical and nutraceutical compositions, the egg yolk containing specific antibodies may be used as an ingredient in foods such as breads, dairy products, margarine, mayonnaise, dressings, sauces, or any other food product which may include eggs or egg yolks as an ingredient.

The compositions may comprise dosage forms for oral administration which include a formulation in which the antibodies are contained within an enteric coating that allows delivery of the active agent to the intestine. The formulations containing specific antibodies may be encapsulated in a dried form or in a liquid form, designed to resist digestion in acidic stomach conditions and to be delivered to affected areas of the intestine. The preferred effective amount of the antibody used in the preparations is about 30 mg daily, most favourably about 10 mg per meal prior to ingestion. The preparation can be used to treat patients with celiac disease by oral administration daily.

The anti-gluten antibodies preferably are administered in the form of physiologically acceptable compositions comprising physiologically acceptable carriers, excipients and/or diluents. Such carriers are nontoxic to recipients at the dosages and concentrations employed. Compositions suitable for in vivo administration may be formulated according to methods well-known in the art. Components that are commonly employed in such formulations include those described in Remington's Pharmaceutical Sciences, 20th ed., 2000, Mack Publishing Company. Ordinarily, the preparation of such compositions entails combining the therapeutic agent with buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and other stabilizers and excipients. Neutral buffered saline or saline mixed with non-specific serum albumin are exemplary appropriate diluents. If desired, the therapeutic agent may be formulated as a lyophilizate using appropriate excipient solutions such as sucrose as a diluent. Appropriate dosages can be determined in standard dosing trials, and may vary according to the chosen route of administration. In accordance with appropriate industry standards, preservatives may also be added, such as benzyl alcohol. In another embodiment, an anti-gluten antibody is administered in another convenient form, such as a food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, the present compositions can be formulated into cereals, snack items such as chips, bars, gum drops, chewable candies or slowly dissolving lozenges.

EXAMPLES

The following examples are intended solely to illustrate embodiments of the invention and are not intended to limit the scope of the claimed invention.

Example 1

Preparation of Anti-Gluten Egg Yolk Antibodies

A first group of laying hens was injected with the gliadin at a concentration of 1.25 mg in a mixture of saline solution (0.5 ml per hen) and Freund's incomplete adjuvant or a flax oil (0.5 ml per hen). A second group of laying hens was injected with the HMG at a concentration of 1.25 mg in a mixture of saline solution (0.5 ml per hen) and Freund's incomplete adjuvant or a flax oil (0.5 ml per hen). A third group of laying hens was injected with the HMG at a concentration of 1.25 mg in a mixture of saline solution (0.5 ml per hen) and Freund's incomplete adjuvant or a flax oil (0.5 ml per hen). A fourth group of laying hens was injected with the cocktail of gluten proteins containing gliadin (0.42 mg), HMG (0.42 mg) and LMG (0.42 mg) at a concentration of 1.26 mg in a mixture of saline solution (0.5 ml per hen) and Freund's incomplete adjuvant or a flax oil (0.5 ml per hen).

In each case, the antigenic materials are injected into subcutaneous skin sites on the neck of laying hens. After two weeks, each group of laying hens is injected again with the same formulations as above to boost the immunity of laying hens.

Figure 2:
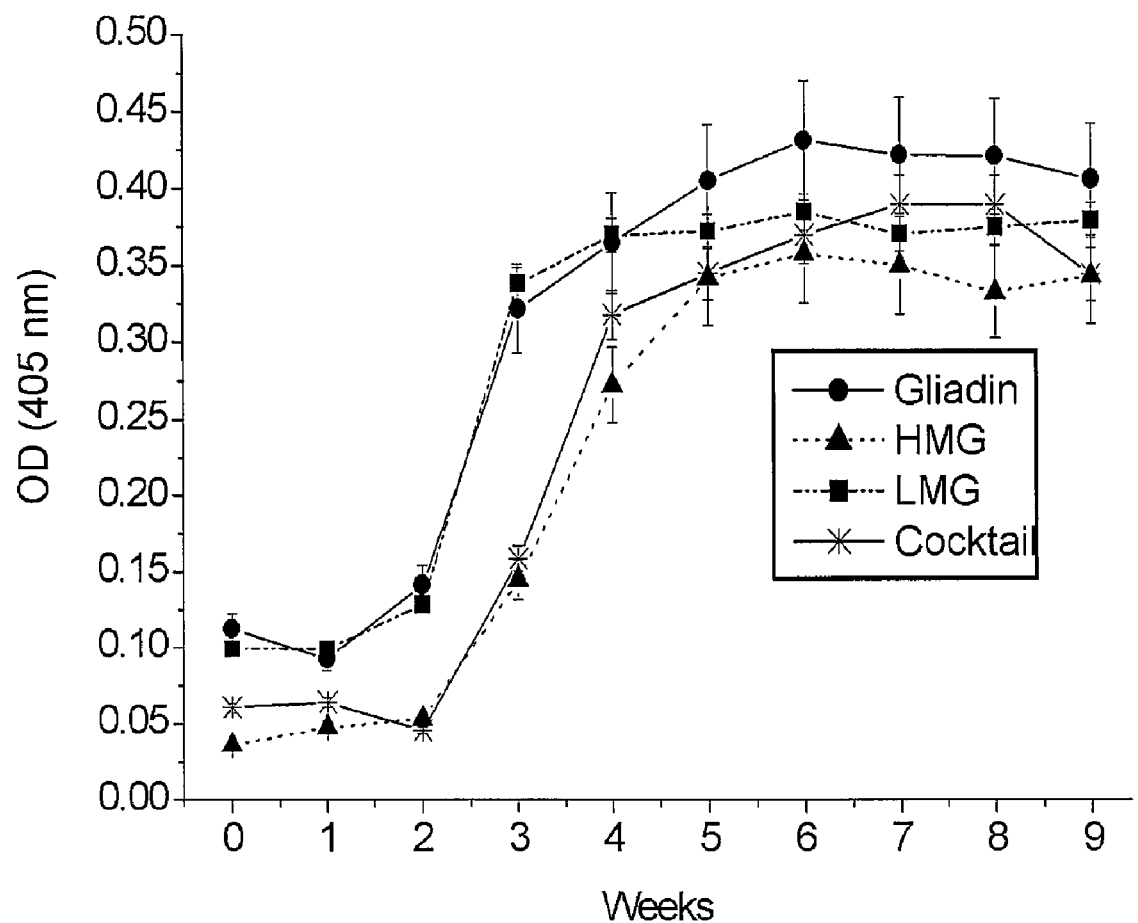
FIG. 2 is a line graph showing a titer of antibodies from egg yolk of hyperimmunized laying hens during the immunization period.

Specific activities of IgY in the egg yolk from laying hens hyperimmunized with gluten proteins were monitored by an indirect ELISA during the immunization period as shown in FIG. 2. The specific gliadin, HMG and LMG IgY activities are detected on day 0, rapidly increase from week 2 to week 4 and thereafter remain relatively high, showing no considerable decline up to 9 weeks. The specific anti-cocktail of gluten protein IgY activity also shows the similar pattern. As a result, a significant amount of IgY specific against gluten proteins are obtained from egg yolks from laying hens which are fed with wheat grains in feed formulation without immunization. However, 4- to 8 fold of specific antibodies are obtained from hyperimmunized laying hens after 4 weeks of initial immunization.

As shown in FIG. 2, eggs containing high levels of specific IgY against gluten proteins are collected during the immunization period of 5 to 8 weeks and were then pooled to determine the amount of antibodies by ELISA. Egg yolks containing non-specific IgY were also prepared as a control. The concentrations of total and specific IgY in the collected egg yolks are assessed by ELISA and shown in TABLE 1.

TABLE 1

The concentrations of total IgY and specific IgY in egg yolk prepared from the hyperimmunized laying hens to gluten proteins.

| | Concentration (mg/ml) | | |
|---|---|---|---|
| | Total IgY | Specific IgY | Percentage (%) |
| Gliadin | 12.5 | 0.88 | 7.0 |
| HMG | 12.1 | 0.79 | 6.5 |
| LMG | 11.3 | 0.81 | 7.2 |
| Cocktail | 12.9 | 1.05 | 8.1 |
| Control | 10.5 | 0.11 | 1.05 |

Example 2

Thermal Stability

Whole egg yolk or purified IgY (containing 240 μg IgY) was thermally treated at various temperatures (4, 20, 37, 62 and 85° C.) for 30 min (TABLE 2). The antibody content in egg yolk IgY decreases with increasing temperature. The residual IgY content in PBS is sharply decreased by 8%, when the IgY samples are thermally treated at 85° C. and the treatment lasted for 30 min. However the residual IgY was quite stable when thermally treated at temperature below 62° C. The components other than IgY in the egg yolk appeared to be significantly effective in protecting the IgY from thermal denaturation at 62° C. Therefore, IgY products should not be thermally exposed beyond 75° C. It is a safe temperature region of commercial practice for egg pasteurization.

TABLE 2

The stability of egg yolk IgY (equivalent to 240 μg IgY) after incubating at various thermal treatments for 30 min.

| Temperature (° C.) | Whole Egg Yolk IgY Content (μg) | Purified IgY Content (μg) |
|---|---|---|
| 4 | 239.9 | 239.9 |
| 20 | 238.9 | 238.9 |
| 37 | 237.6 | 235.7 |
| 62 | 233.1 | 234.7 |
| 85 | 19.7 | 15.9 |

Example 3

Acid Stability

Whole egg yolk or purified IgY (containing 240 μg IgY) was treated at various acidic conditions (pH 2 to 7 in PBS) at 37° C. for 2 hours (TABLE 3). After incubation, the solution was neutralized by 100 fold dilutions with PBS containing 0.05% Tween™ 20. Residual IgY content after various acidic treatments were concentrated by ELISA. The antibody content in whole egg yolk and purified IgY decreased with higher acidic conditions. The residual IgY content in PBS was decreased by more than 70%, when the IgY samples were treated at pH 2. However at higher than pH 3, IgY was relatively stable. The antibody content in egg yolk decreases with higher acidic conditions. The residual IgY content in the whole egg yolk decreases by more than 70%, when the whole egg yolk is treated at pH 2. However the residual IgY in the egg yolk is stable at over pH 3. Therefore, it appears to be important that IgY should not be subjected to acidic conditions at a pH less than 3 in food processing or storage.

TABLE 3

The stability of egg yolk IgY (equivalent to 240 μg IgY) after incubating at various acidic conditions at 37° C. for 2 h.

| pH conditions | Whole Egg Yolk IgY Content (μg) | Purified IgY Content (μg) |
|---|---|---|
| 2 | 108.2 | 88.8 |
| 3 | 208.3 | 192.1 |
| 4 | 230.1 | 223.8 |
| 5 | 239.8 | 228.4 |
| 6 | 235.7 | 236.9 |
| 7 | 233.1 | 238.8 |

Example 4

Protease Stability

Whole egg yolk or purified IgY (containing 240 μg IgY) was diluted with 50 mM Tris buffer (pH 7.0) and then homogenized at 1,500 rpm for 3 min (TABLE 4). Trypsin (Sigma) was dissolved at a concentration of 1 mg/mL of the Tris buffer and the IgY solution was mixed with the enzyme solution (1:9), and the mixtures were incubated at 37° C. for time periods from 0 to 4 hours. A 0.5 mL sample of the incubation mixture was mixed with 0.05 mL of phenylmethyl sulfonyl fluoride solution (10 mM in isopropanol) to inactivate the enzyme. The remaining antibody activity was measured by ELISA. There is some degree of hydrolysis of IgY but significant portion of IgY activity is survived during harsh 4 hour digestion period. This may be worthy noting that antibodies in egg yolk are more resistant to enzymatic breakdown in comparison with IgY in a pure form. It is likely that the extra egg yolk proteins and lipids play a protecting role against enzymatic attack. It is evident that IgY is vulnerable toward enzymatic hydrolysis during relatively extended duration. However, a significant portion of IgY survives a 4 hour digestion time period. This time factor is important to use IgY in food processing and oral application.

TABLE 4

The stability of egg yolk IgY (equivalent to 240 μg IgY) after incubating with trypsin at 37° C. for 1-4 h.

| Incubation time (h) | Whole Egg Yolk IgY Content (μg) | Purified IgY Content (μg) |
|---|---|---|
| 0 | 240 | 240 |
| 1 | 199.3 | 178.9 |
| 2 | 177.2 | 131.8 |
| 4 | 152.9 | 102.7 |

Example 5

In Vivo Stability

As IgY is a protein, it is possible that a significant amount of IgY given orally will be degraded and inactivated in the stomach and small intestine. However, the other components of egg yolk may have some protective effect. We have attempted to examine the remaining total IgY content in stomach and small intestine after feeding whole egg yolk powder for various times (30 min, 1 h, 2 h, 4 h, 24 h and control groups) by using mice as an animal model. The result of residual IgY after feeding egg yolk powder to mice is shown in TABLE 5.

Twenty four albino mice (four mice per group) were fasted overnight before feeding. Dried egg yolk powder was continuously fed to mice ad libitum with free access to water. After ½, 1, 2, 4 and 24 hour, mice were terminated and dissected for the stomach and small intestine. The tissues were homogenized with buffer solution to neutralize the pH and enzyme activity with enzyme inhibitors and then centrifuged to collect supernatant including antibodies. The antibodies were concentrated by salt precipitation. The antibody activity was expressed by milligram of egg yolk antibody per gram of tissue. The control mice were also terminated before feeding as a control.

Yolk powder contains about 18 mg of IgY per gram of egg yolk powder. After dissecting tissues from mice, the stomach and small intestine after removing digesta were measured. The wet weight of stomach is approximately 0.07-0.11 g. The wet weight of small intestine is approximately 0.50-0.58 g. For large intestine, the wet weight is 0.22-0.28 g. The weight of egg yolk powder in stomach is approximately ranged from 0.3-0.6 g. The weight of digesta in SI, 0.18-0.44 g. If IgY were not digested, total IgY content is approximately 90 mg/gram of stomach tissue and total IgY content is approximately 9 mg per gram of SI tissue.

TABLE 5

The concentrations of total IgY and specific IgY of yolks after feeding egg yolk powder to mouse.

Stomach

| Group | Feeding period | Average IgY Ingested (mg) | Total IgY, mg/g of tissue |
|---|---|---|---|
| A | 30 min | 7.02 | 4.72 ± 1.21 |
| B | 1 hour | 7.83 | 8.22 ± 1.62 |
| C | 2 hour | 12.60 | 9.20 ± 1.42 |
| D | 4 hour | 20.61 | 9.60 ± 1.34 |
| E | 24 hour | 36.72 | 28.20 ± 3.25 |

Small Intestine

| Group | Feeding period | Total IgY, mg/g of tissue |
|---|---|---|
| A | 30 min | 0.48 ± 0.08 |
| B | 1 hour | 0.44 ± 0.11 |
| C | 2 hour | 0.42 ± 0.10 |
| D | 4 hour | 0.39 ± 0.07 |
| E | 24 hour | 0.51 ± 0.06 |

Example 6

Testing of Anti-Gluten Antibody Composition Under Simulated Gut Conditions

Four gluten proteins from wheat, barley, rye and oat were isolated using the method described by Tatham et al. (2000). The gluten proteins, which are active in celiac disease and other gluten related conditions, were isolated as prolamins (known as gliadins in wheat, hordeins in barley, secalins in rye and avenins in oat). Two hundred 35-wk-old Single Comb White Leghorn chickens were immunized four times with emulsions of the extracted gluten proteins until hens produced egg yolks with a high titer of specific IgY. A therapeutic composition comprising IgY polyclonal antibodies and a physiologically acceptable excipient was prepared and formed into an oral dosage form (in this embodiment, a capsule). The stability and dissolution of the composition under simulated gut conditions were determined in several tests summarized below.

a) Stability Test:

IgY contents in capsules with or without excipient (for example, mannitol or sorbitol) maintain a constant amount of IgY up to 50 weeks at room temperature (Table 6):

TABLE 6

Long term stability of IgY capsule

Figure 3:
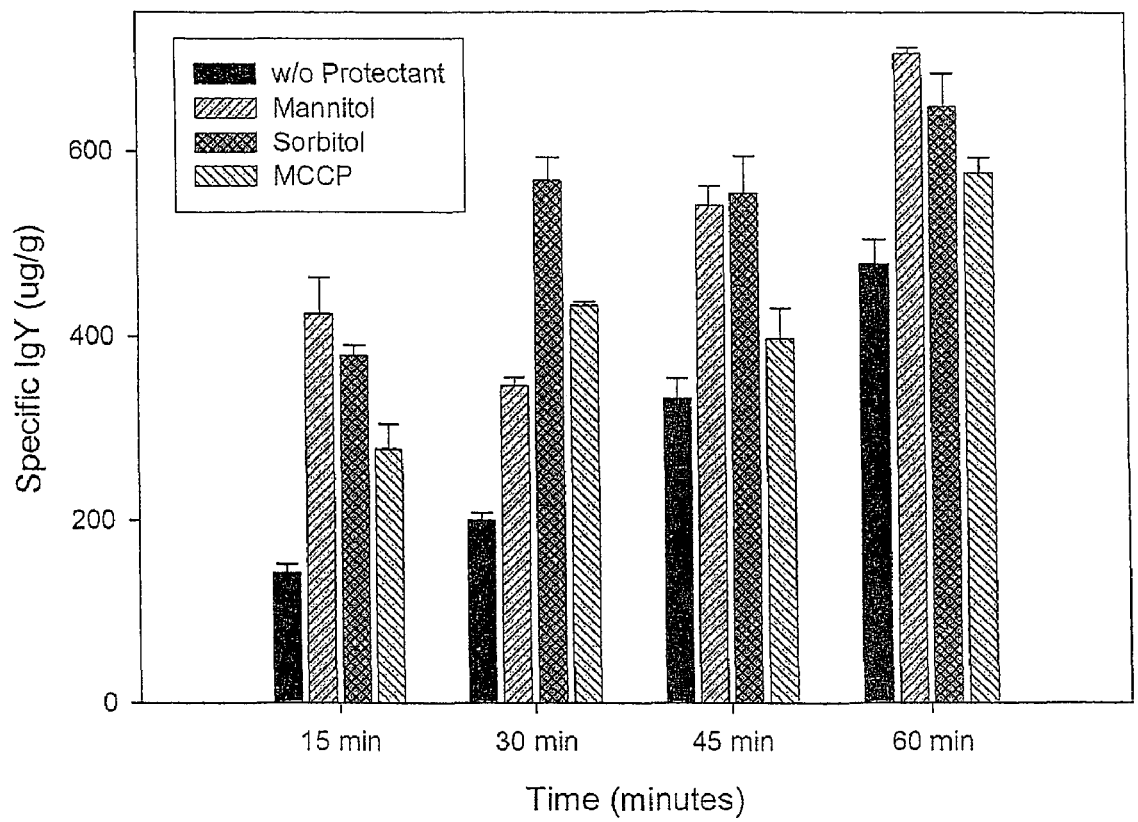
FIG. 3 is a bar graph showing the survival of IgY over time in simulated gut fluid.

| Content (mg/ml) | Week no. | 0% | 5% | 10% | 15% | 20% |
|---|---|---|---|---|---|---|
| IgY | 1 | 23.59 | 22.86 | 21.43 | 22.78 | 22.74 |
| | 2 | 31.37 | 30.86 | 35.13 | 36.57 | 38.71 |
| | 3 | 22.71 | 25.96 | 25.16 | 27.48 | 26.24 |
| | 4 | 24.56 | 26.59 | 28.93 | 30.50 | 31.18 |
| | 25 | 22.51 | 23.00 | 26.48 | 23.68 | 24.99 |
| | 50 | 24.28 | 26.26 | 28.13 | 28.86 | 28.58 | b) Disintegration Test:

The IgY capsule was studied for disintegration under gastric pH of 1.2. All six capsules were observed to rupture after 2.5 min in the disintegration vessel, whereas a complete disintegration of the six capsules was observed after 30 minutes of exposure. This result suggests that IgY can be released for mixture with the food matrix to bind target gluten.

c) Dissolution Test:

Compositions comprising IgY polyclonal antibodies and an excipient (20% mannitol, 20% sorbitol or 15% microcrystalline cellulose powder) were used to test the survival of IgY polyclonal antibodies in simulated gut fluid (SGF) and intestinal fluid containing bile salt (SIF). In SGF, the activity of IgY with either mannitol or sorbitol was higher than IgY without excipient and MCCP (FIG. 3). IgY without excipient shows the lowest activity of IgY, indicating that excipient protects IgY from enzymatic digestion and low gastric pH. Food normally resides for about one hour in the stomach. After a one hour exposure, the survival rate of IgY was highest at 70.5% and 64.85% in mannitol and sorbitol, respectively. This result suggests that excipient addition may be beneficial and that sufficient IgY remains to enter the small intestine.

After a one hour incubation of IgY with sorbitol in SIF, IgY was degraded. The activity of IgY was retained at 24.1% of total IgY. Overall, the dissolution results support the survival of IgY polyclonal antibodies in the gastrointestinal tract after ingestion, there by allowing the opportunity for IgY polyclonal antibodies to capture gluten in both the stomach and small intestine.

d) In Vitro Assessment of Anti-Gliadin Antibody Activity

Anti-gliadin IgY activity was evaluated to determine 100% inhibition of gliadin by in vitro incubation of IgY capsule and gliadin in gastrointestinal fluid (SGF and SIF). This test estimates the binding ratio of IgY antibody and gliadin under physiological conditions which in turn, determines the dose of IgY antibody to inhibit gliadin in the gastrointestinal tract of gluten-intolerant subjects. A competitive assay of gliadin versus IgY capsule showed that 0.08 g of IgY captured 0.3 g of gliadin in SGF. A competitive assay of gliadin versus IgY capsule showed that 0.08 g of IgY captured 0.015 g of gliadin in the SIF. Two IgY capsules (800 mg IgY formula) may thus neutralize 3 g and 0.15 g of gliadin peptides in simulated stomach and small intestine, respectively.

IgY binding capacity in complex meal conditions was also investigated. Food spiked with gliadin, and IgY capsule were mixed in stomach and small intestine simulated conditions. A competitive assay of gliadin in 10 g of food matrix versus IgY capsule showed that 0.08 g of IgY captured 0.28 g of gliadin in the food matrix in SGF. A competitive assay of gliadin in the food matrix versus IgY capsule showed that 0.08 g of IgY captured 0.24 g of gliadin in the food matrix. This result suggests that IgY formula with foods was less damaged in the small intestine due to the diluted effect of protein digestive enzymes in SIF.

The above results indicate that two IgY capsules (800 mg IgY composition) can neutralize 3.2 gram of gliadin in foods in simulated stomach and small intestine, respectively. Based on 70% survival of IgY in stomach, two IgY capsules may bind to 2.8 g of gliadin in foods and the remaining IgY may also bind to 2.4 g of gliadin in small intestine, which indicates that two capsules of IgY may bind 5.2 g of gliadin in both stomach and small intestine.

The above experiments demonstrate that the IgY compositions exhibit the activity of being capable of specifically binding to gluten in simulated gastrointestinal tract fluids. Further, the inclusion of an excipient also enhances the survival of IgY polyclonal antibodies in simulated gastrointestinal fluids.

Example 7

Testing of Anti-Gluten Antibody Composition in a Murine Model

The ability of the anti-gluten IgY composition in preventing gliadin from traversing the intestinal epithelium was tested. A murine model was used to validate the effect of IgY antibodies against gluten peptides extracted from wheat grains. The results show that the IgY composition captures gliadin in the stomach and small intestine, resulting in no absorption of gliadin into the system.

One hundred and twenty-eight 20-day-old BALB/c mice were cared for in accordance with the Canadian Council on Animal Care Guidelines and Policies. For statistical analysis, eight mice were allocated to each treatment group. Mice were fed the following diets: A) 100 mg of gliadin; B) 100 mg of gliadin and 1 mg of IgY formula; C) 100 mg of gliadin and 5 mg of IgY formula; and D) 100 mg of IgY formula. The animals were euthanized at 12 hours after meal intake. Thirty-two 20-day-old BALB/c mice were used each week for a duration of four weeks. The stomach, small intestine and large intestine were collected for gliadin content. The measurement of gliadin was assayed using a Gliadin ELISA Kit (IM 3717, Immunotech). Results are shown in Table 7A-C, where the average gliadin remaining in the GI tract contents was measured.

TABLE 7

The concentrations of gliadin in the gastrointestinal tract after 12 hours feeding

| | Diet | | |
|---|---|---|---|
| Group | Gliadin (mg) | IgY Formula (mg) | Average gliadin remaining (mg) |
| A. Stomach | | | |
| A | 100.0 | 0.0 | 0.0 |
| B | 100.0 | 1.0 | 0.0 |
| C | 100.0 | 5.0 | 0.0 |
| D | 0.0 | 100.0 | 0.0 |
| B. Small intestine | | | |
| A | 100.0 | 0.0 | 22.2 |
| B | 100.0 | 1.0 | 19.5 |
| C | 100.0 | 5.0 | 20.7 |
| D | 0.0 | 100.0 | 0.0 |
| C. Large Intestine | | | |
| A | 100.0 | 0.0 | 35.0 |
| B | 100.0 | 1.0 | 64.8 |
| C | 100.0 | 5.0 | 78.6 |
| D | 0.0 | 100.0 | 0.0 |

In Table 7D, the data in the right hand column represents the amount of gliadin absorbed by the GI tract tissue, which was determined by subtracting the amount recovered from the GI tract contents from the amount ingested by the animal.

| D. Ingestion of Gliadin | | | |
|---|---|---|---|
| | Diet | | |
| Group | Gliadin (mg) | IgY Formula (mg) | Feed-stomach-small intestine-large intestine remaining (mg) |
| A | 100.0 | 0.0 | 42.8 |
| B | 100.0 | 1.0 | 15.7 |
| C | 100.0 | 5.0 | >1.0 |
| D | 0.0 | 100.0 | 0.0 |

As can be seen in Table 7, the IgY formula increased the amount of gliadin remaining in the GI tract, and decreased the amount of gliadin absorbed by the GI tract tissue.

Gliadin, high molecular glutenin and low molecular glutenin act as modulators of permeability in intestinal epithelium in those suffering from celiac disease. Permeation of gluten into the mucosal membrane of the intestine is required for celiac disease toxicity. Thus, by binding to the gliadin, HMG and LMG of gluten, with anti-gluten antibodies, the gluten is passed through the intestines, rather than being transported into the mucosal membrane, thereby preventing or minimizing the disease-causing toxicity. The overall results of the above animal study demonstrate that the anti-gluten IgY composition immobilized gliadin in the gastrointestinal tract, sequestering gliadin from exposure to the intestinal lining.

In addition, the anti-gluten IgY composition blocks the absorption of gliadin in the small intestine to prevent a cascade of inflammatory events. Gluten in foods can be absorbed into the systemic blood vessels through the digestive system. The absorbed gluten can activate immune reactions, starting with an IgA response. IgA is the principal immunoglobulin in secretions from the intestinal mucosa and provides protection against antigens at mucosal surfaces.

The blood of animals within Groups A-D was further tested to measure the levels of IgA antibody, thereby determining whether gliadin was absorbed into the system:

TABLE 8

| | Diet | | |
|---|---|---|---|
| Group | Gliadin (mg) | IgY Formula (mg) | Absorbance (OD-650 nm) |
| | IgA antibody titer | | |
| A | 100.0 | 0.0 | 0.245 |
| B | 100.0 | 1.0 | 0.0 |
| C | 100.0 | 5.0 | 0.0 |
| D | 0.0 | 100.0 | 0.0 |

In Groups B, C and D which were administered varying amounts of the anti-gluten IgY composition, there was no IgA antibody in the blood. However, Group A which consumed only gliadin contained IgA antibody in the blood. These results suggest that the anti-gluten IgY composition blocks the absorption of gliadin in the small intestine, thereby preventing undesirable immune reactions.

As will be apparent to those skilled in the art, various modifications, adaptations and variations of the foregoing specific disclosure can be made without departing from the scope of the invention claimed herein. The various features and elements of the described invention may be combined in a manner different from the combinations described or claimed herein, without departing from the scope of the invention.

The invention claimed is:

1. A method of treating or ameliorating the symptoms of celiac disease or a gluten sensitive condition comprising the step of administering to a mammal in need thereof a pharmaceutical or nutraceutical composition or food product comprising anti-gluten IgY antibodies.

2. A method of preventing gluten uptake in the digestive system of a mammal comprising the step of administering to the mammal a pharmaceutical or nutraceutical composition or a food product comprising anti-gluten IgY antibodies.

3. The method of claim 1 wherein the anti-gluten egg yolk antibodies comprises polyclonal antibodies specific to gliadin, high molecular glutenin (HMG), or low molecular glutenin (LMG).

4. The method of claim 3, wherein the polyclonal antibodies are prepared by (a) immunizing an egg-laying fowl with one or more of gliadin, HMG, and LMG, (b) collecting eggs from the immunized fowl, (c) preparing the composition from the egg yolk or IgY purified from the egg yolk.

5. The method of claim 1 wherein the pharmaceutical or nutraceutical composition or food product comprises egg yolk comprising anti-gluten IgY antibodies.

6. The method of claim 5 wherein the egg yolk is liquid or dried, and formed into an oral dosage form.

7. The method of claim 5 wherein the pharmaceutical or nutraceutical composition comprises a beverage.

8. The method of claim 2 wherein the anti-gluten egg yolk antibodies comprises polyclonal antibodies specific to gliadin, high molecular glutenin (HMG), or low molecular glutenin (LMG).

9. The method of claim 8, wherein the polyclonal antibodies are prepared by (a) immunizing an egg-laying fowl with one or more of gliadin, HMG, and LMG, (b) collecting eggs from the immunized fowl, (c) preparing the composition from the egg yolk or IgY purified from the egg yolk.

10. The method of claim 2 wherein the pharmaceutical or nutraceutical composition or food product comprises egg yolk comprising anti-gluten IgY antibodies.

11. The method of claim 10 wherein the egg yolk is liquid or dried, and formed into an oral dosage form.

12. The method of claim 10 wherein the pharmaceutical or nutraceutical composition comprises a beverage.

* * * * *